US006528312B1

(12) United States Patent
Braun (10) Patent No.: US 6,528,312 B1
(45) Date of Patent: Mar. 4, 2003

(54) USE OF G-ACTIN FOR IMPROVING TRANSFECTION OF A POLYNUCLEOTIDE INTO A CELL

(75) Inventor: Serge Braun, Dorlisheim (FR)

(73) Assignees: Transgene S.A., Strasbourg (FR); Association Francaise Contre les Myopathies, Paris (FR)

( * ) Notice: Subject to any disclaimer, the term of this patent is extended or adjusted under 35 U.S.C. 154(b) by 0 days.

(21) Appl. No.: 09/462,289

(22) PCT Filed: May 5, 1999

(86) PCT No.: PCT/EP99/03082

§ 371 (c)(1),
(2), (4) Date: Mar. 20, 2000

(87) PCT Pub. No.: WO99/56784

PCT Pub. Date: Nov. 11, 1999

(30) Foreign Application Priority Data

May 6, 1998 (EP) ............................................. 98401108
Jul. 2, 1998 (EP) ............................................. 98401667

(51) Int. Cl.$^7$ ................................................ C12N 15/63
(52) U.S. Cl. ........................ 435/455; 435/456; 435/458; 435/325; 424/1.13; 514/2; 514/44
(58) Field of Search ...................... 514/44, 2; 435/455, 435/456, 458, 325; 424/1.13

(56) References Cited

U.S. PATENT DOCUMENTS

| 5,506,128 A | * | 4/1996 | Cochran et al. | ......... 435/235.1 |
| 5,714,166 A | * | 2/1998 | Tomalia et al. | ............. 424/486 |
| 5,908,635 A | * | 6/1999 | Thierry | ....................... 424/450 |

FOREIGN PATENT DOCUMENTS

| WO | 95 26718 | 10/1995 |
| WO | 98 06437 | 2/1998 |
| WO | 98 08947 | 3/1998 |
| WO | 98 17799 | 4/1998 |

OTHER PUBLICATIONS

Inder M. Verma et al., Gene therapy—promises, problems and prospects, Nature, vol. 389, pp. 239–242.*
W. French Anderson, Human gene therapy, Nature, vol. 392, pp. 25–30.*
Stuart H. Orkin, M.D. et al., Report and recommendations of the panel to assess the nih investment in research on gene therapy, pp. 1–38.*
Erich WFW Alton et al., Prospects for respiratory gene therapy, British Journal of Hospital Medicine, 1997, vol. 58, No. 1, p. 47–.*
Richard C. Boucher, Current status of CF gene therapy, TIG, Mar. 1996, vol. 12, No. 3, pp. 1–4.*
Richard C. Boucher, Status of gene therapy for cystic fibrosis lung disease, The Journal of Clinical Investigation, Feb. 1999, vol. 103, No. 4, pp. 441–445.*

Melissa A. Rosenfield, M.D. et al., Gene Therapy for Cystic Fibrosis, CHEST/109/1/Jan., 1996, pp. 241–252.*
Toshifumi Hara et al., Receptor–mediated transfer of pSV2CAT DNA to a human hepatoblastoma cell line HepG2 using asialofetuin–labeled cationic liposomes, Gene, 159, 1995, pp. 167–174.*
Charles M. Rice et al., Production of Infectious RNA Transcripts from Sindbis Virus cDNA Clones: Mapping of Lethal Mutations, Rescue of a Temperature Sensitive Marker, and In Vitro Mutagenesis To Generate Defined Mutants, pp. 3809–3819.*
Leann Tilley et al., Solubilization of Native Actin Monomers from Human Erythrocyte Membranes, Aust. J. Biol. Sci. 1986, 39, pp. 117–124.*
Edda Ballwebber et al., Induction of the polymerization of actin from the actin: thymosin B4 complex by phalloidin, skeletal myosin subfragment 1, chicken intestinal myosin I and free ends of filamentous actin, Eur. J. Biochem. 223, pp. 419–426.*
Hiroshi Nakayasu et al., Association of Actin with the nuclear matrix from bovine lymphocytes, Experimental Cell Research, 143, pp. 55–62.*
Ingrid Blikstad et al., Selective Assay of Monomeric and Filamentous Actin in Cell Extracts, Using Inhibition of Deoxyribonuclease I, Cell, vol. 15, pp. 935–943.*
Rikin A. Trivedi et al., Liposome–Mediated Gene Transfer into Normal and Dystrophin–Deficient Mouse Myoblasts, Journal of Neurochemistry, pp. 2230–2238.*
J. Rosenecker et al., Towards Gene Therapy of Cystic Fibrosis, Eur. J. Med. Res. (1998) 3: pp. 149–156.*
Jane C. Davies et al., Prospects for gene therapy for cystic fibrosis, Molecular Medicine Today, pp. 292–299.*
Kensuke Yonemura et al., A New Assay Method for DNase Fluorescence Polarization and Fluorescence Intensity Using DNA–Ethidium Bromide Complex as a Sensitive Substrate, J. Biochem. vol. 92, pp. 1297–1303.*
George Karpati et al., The principles of gene therapy in Duchenne muscular dystrophy, Clin. Invest. Med., vol. 17:5, pp. 499–509.*
Matt Cotton et al., Transferrin–polycation–mediated introduction of DNA into human leukemic cells: Stimulation by agents that affect the survival of transfected DNA or modulate transferrin receptor levels, Proc. Natl. Acad. Sci. USA, vol. 87, pp. 4033–4040.*
Leona P. Whichard et al., The Effect of Chloroquine on the Enzymatic Hydrolysis of Nucleic Acids, Molecular Pharmacology, 6, pp. 548–556.*

(List continued on next page.)

Primary Examiner—James Ketter
Assistant Examiner—Richard A Schnizer
(74) Attorney, Agent, or Firm—Burns, Doane, Swecker & Mathis, L.L.P.

(57) ABSTRACT

Described is the use of a nuclease inhibitor or of interleukin-10 (IL-10) for the preparation of a therapeutic composition for improving transfection of a polynucleotide into a cell, and to compositions comprising a mixture of polynucleotide and nuclease inhibitor and/or interleukin-10.

26 Claims, 5 Drawing Sheets

OTHER PUBLICATIONS

T. Maniatis et al., Molecular Cloning, pp. 92–94.*

Chissoe s. et al., Homo sapiens, NCBI Sequence Viewer, pp. 1–2.*

Mandel, J. L. et al., Gallus gallus, NCBI Sequence Viewer, pp. 1–2.*

Ramon et al: "Aurintricarboxylic Acid As a Nuclease Inhibitor in Fungal Protoplasts", FEMS Microbiology Letters, vol. 36, 1986, pp. 9–13, XP002080133, the whole document.

Pinder et al: "Investigation of the Actin–Deoxyribonulcease I Interaction Using a Pyrene–Conjugated Actin Derivative", Biochemistry, vol. 21, 1982, pp. 4886–4890, XP002080134, cited in the application, p. 4886, abstract.

Morgan J.E.: "Cell and Gene Therapy in Duchenne Muscular Dystrophy" Human Gene Therapy, vol. 5, No. 2, Feb. 1994, pp. 165–173, XP000610675, p. 165, abstract.

McLachlan G. et al, "Evaluation in Vitro and in Vivo of Cationic Liposome–Expression Construct Complexes for Cystic Fibrosis Gene Therapy", Gene Therapy, vol. 2, No. 9, Nov. 1995, pp. 614–622, XP000670837, p. 614, abstract.

Howard M. et al, "Biological Properties of Interleukin 10", Journal of Clinical Immunology, US, Plenum Publishing Co., vol. 12, No. 4, pp. 239–247, XP002060141, ISSN: 0271–9142, p. 242, paragraph 3, p. 245, paragraph 3.

* cited by examiner

USE OF G-ACTIN FOR IMPROVING TRANSFECTION OF A POLYNUCLEOTIDE INTO A CELL

The present invention relates to the use of a nuclease inhibitor or of interleukin-10 (IL-10) for the preparation of a therapeutic composition for improving transfection of a polynucleotide into a cell, and to compositions comprising a mixture of polynucleotide and nuclease inhibitor and/or interleukin-10. Such a composition is useful in gene therapy, vaccination, and any therapeutic situation in which a gene-based product is administered to cells in vivo.

Gene therapy has generally been conceived as principally applicable to heritable deficiency diseases (cystic fibrosis, dystrophies, haemophilias, etc.) where permanent cure may be effected by introducing a functional gene. However, a much larger group of diseases, notably acquired diseases (cancer, AIDS, multiple sclerosis, etc.) might be treatable by transiently engineering host cells to produce beneficial proteins.

Applications are, for example, the treatment of muscular dystrophies or of cystic fibrosis. The genes of Duchenne/Becker muscular dystrophy and cystic fibrosis have been identified and encode polypeptides termed dystrophin and cystic fibrosis transmembrane conductance regulator (CFTR), respectively. Direct expression of these genes within, respectively, the muscle or lung cells of patients should contribute to a significant amelioration of the symptoms by expression of the functional polypeptide in targeted tissues. Moreover, studies in cystic fibrosis have suggested that one would need to achieve expression of the CFTR gene product in only about 5% of lung epithelial cells in order to significantly improve the pulmonary symptoms.

Another application of gene therapy is vaccination. In this regard, the immunogenic product encoded by the polynucleotide introduced in cells of a vertebrate may be expressed and secreted or be presented by said cells in the context of the major histocompatibility antigens, thereby eliciting an immune response against the expressed immunogen. Functional polynucleotides can be introduced into cells by a variety of techniques resulting in either transient expression of the gene of interest, referred to as transient transfection, or permanent transformation of the host cells resulting from incorporation of the polynucleotide into the host genome.

Successful gene therapy depends on the efficient delivery to and expression of genetic information within the cells of a living organism. Most delivery mechanisms used to date involve viral vectors, especially adeno- and retroviral vectors. Viruses have developed diverse and highly sophisticated mechanisms to achieve this goal including crossing of the cellular membrane, escape from lysosomal degradation, delivery of their genome to the nucleus. Consequently, viruses have been used in many gene delivery applications in vaccination or gene therapy applied to humans. The use of viruses suffers from a number of disadvantages: retroviral vectors cannot accommodate large-sized DNA (for example, the dystrophin gene which is around 13 Kb), the retroviral genome is integrated into host cell DNA and may thus cause genetic changes in the recipient cell and infectious viral particles could disseminate in the organism or in the environment and adenoviral vectors can induce a strong immune response in treated patients (Mc Coy et al., Human Gene Therapy 6 (1995), 1553–1560; Yang et al., Immunity 1 (1996), 433–442). Nevertheless, despite these drawbacks, viral vectors are currently the most useful delivery systems because of their efficiency. Non-viral delivery systems have been developed which are based on receptor-mediated mechanisms (Perales et al., Eur. J. Biochem. 226 (1994), 255–266; Wagner et al., Advanced Drug Delivery Reviews 14 (1994), 113–135), on polymer-mediated transfection such as polyamidoamine (Haensler and Szoka, Bioconjugate Chem. 4 (1993), 372–379), dendritic polymer (WO 95/24221), polyethylene imine or polypropylene imine (WO 96/02655), polylysine (U.S. Pat. No. 5,595,897 or FR 2 719 316) or on lipid-mediated transfection (Feigner et al., Nature 337 (1989), 387–388) such as DOTMA (Feigner et al., Proc. Natl. Acad. Sci. USA 84 (1987), 7413–7417), DOGS or Transfectam™ (Behr et al., Proc. Natl. Acad. Sci. USA 86 (1989), 6982–6986), DMRIE or DORIE (Felgner et al., Methods 5 (1993), 67–75), DC-CHOL (Gao and Huang, BBRC 179 (1991), 280–285), DOTAP™ (McLachlan et al., Gene Therapy 2 (1995), 674–622) or Lipofectamine™. These systems present potential advantages with respect to large-scale production, safety, targeting of transfectable cells, low immunogenicity and the capacity to deliver large fragments of DNA. Nevertheless their efficiency in vivo is still limited.

Finally, in 1990, Wolff et al. (Science 247 (1990), 1465–1468) have shown that injection of naked RNA or DNA, without a special delivery system, directly into mouse skeletal muscle results in expression of reporter genes within the muscle cells. This technique for transfecting cells offers the advantage of simplicity and experiments have been conducted that support the usefulness of this system for the delivery to the lung (Tsan et al., Am. J. Physiol. 268 (1995), L1052–L1056; Meyer et al., Gene Therapy 2 (1995), 450–460), brain (Schwartz et al., Gene Therapy 3 (1996), 405–411), joints (Evans and Roddins, Gene therapy for arthritis; In Wolff (ed) Gene therapeutics: Methods and Applications of direct Gene Transfer. Birkhaiser. Boston (1990), 320–343), thyroid (Sikes et al., Human Gen. Ther. 5 (1994), 837–844), skin (Raz et al., Proc. Natl. Acad. Sci. USA 91 (1994), 9519–9523) and liver (Hickman et al., Hum. Gene Ther. 5 (1994),1477–1483). Nevertheless, Davis et al. (Human Gene Therapy 4 (1993), 151–159 and Human Mol. Genet. 4 (1993), 733–740) observed a large variability of expression due to nonuniform distribution of naked DNA injected into skeletal muscle in vivo. Only a small proportion of the muscle fibers (about 1–2%) are transfected and this level of gene transfer would be insufficient for the treatment of primary myopathies. The authors propose solutions in order to obtain an improvement of the efficiency of gene transfer (resulting in about 10% of transfected muscle fibers) by preinjecting muscles with a relatively large volume of hypertonic sucrose or with toxins, for example cardiotoxin isolated from snake, in order to stimulate regeneration of muscles. These methods, although promising, would not be applicable for human treatment.

Thus, the available delivery methods are not satisfactory in terms of safety or efficiency for their implementation in in vivo gene therapy.

Therefore, the technical problem underlying the present invention is the provision of improved methods and means for the delivery of nucleic acid molecules in gene therapy.

This technical problem is solved by the provision of the embodiments as defined in the claims.

Accordingly, the present invention relates to the use of a nuclease inhibitor for the preparation of a therapeutic composition for introducing a polynucleotide into a cell. It was surprisingly found that the addition of a nuclease inhibitor when transfecting a polynucleotide into vertebrate tissue leads to a dramatic improvement of the transfection efficiency. In particular, it was surprisingly found that if the polynucleotide is injected together with a nuclease inhibitor, e.g., into muscular tissue, the transfection is not only improved in the surrounding of the injection site but also in other areas of the muscle. Thus, the present invention preferably relates to the use of a nuclease inhibitor for the preparation of a pharmaceutical composition for an improved introduction of a polynucleotide into a cell. The term "improved introduction" in the scope of the present invention means, in this regard, a more efficient uptake of a polynucleotide by cells when a nuclease inhibitor is present compared to an introduction performed without a nuclease inhibitor. This can be determined by comparing the amount of the polynucleotide taken up without the use of a nuclease inhibitor and comparing this amount with the amount taken up by the cells when using a nuclease inhibitor under the same experimental conditions. Preferably, the improved introduction can be determined by a higher amount of expression of the polynucleotide transferred into the cells when using a nuclease inhibitor in comparison to a situation where no nuclease inhibitor is used.

Preferably, an improved introduction of the polynucleotide into the cell means that the uptake of the polynucleotide by cells is not only improved at the site of administration of the polynucleotide and nuclease inhibitor but is also improved in neighboring cells. Particularly preferred, an improved introduction means that the used nuclease inhibitor shows the same improving effect on the uptake of a polynucleotide by cells as does G-actin when compared to the administration of the polynucleotide without any nuclease inhibitor.

The therapeutic compositions according to the first aspect of the present invention are particularly useful for the delivery of polynucleotides to cells or tissues of a subject in the scope of a gene therapeutic method but are not limited to such use. The term "gene therapy method" is preferably understood as a method for the introduction of a polynucleotide into cells either in vivo or by introduction into cells in vitro followed by re-implantation into a subject. "Gene therapy" in particular concerns the case where the gene product is expressed in a target tissue as well as the case where the gene product is excreted, especially into the blood stream. In the scope of the present invention the term "introduction" means the transfer of the polynucleotide into a cell (transfection).

In the scope of the present invention the term "nuclease" means an enzyme with the capability to degrade nucleic acid molecules. Such nucleases encompass nucleases which can degrade single stranded nucleic acid molecules as well as nucleases which can degrade double stranded nucleic acid molecules. Furthermore, the nuclease can have the capability to degrade RNA or DNA. Preferably, it is a nuclease which degrades DNA. More preferably, the nuclease is a DNAse I, and particularly preferred a human nuclease. A DNAse I in the scope of the present invention is to be understood as an endonuclease that hydrolyzes double-stranded or single-stranded DNA preferentially at sites adjacent to pyrimidine nucleotides. The product of this hydrolysis is a complex mixture of 5'-phosphate mono- and oligonucleotides. In the presence of $Mg^{2+}$, a DNAse I attacks each strand of DNA independently and the sites of cleavage are distributed in a statistically random fashion. Furthermore, in the presence of $Mn^{2+}$, DNAse I cleaves both strands of DNA at approximately the same site to yield fragments of DNA that are blunt-ended or that have protruding termini only one or two nucleotides in length.

In the scope of the present invention a nuclease inhibitor is defined by its capacity to act on a nuclease activity in a way that leads to a total or partial loss of the property of the nuclease to degrade a nucleic acid molecule. This capacity can be determined by incubating the potential inhibitor with the nuclease and with a nucleic acid molecule, which is normally degraded by the nuclease, under conditions which normally allow the nuclease to degrade the nucleic acid molecule and by determining whether the inhibitor represses or decreases the degradation of the nucleic acid molecule. The inhibitor can bind to the nuclease or can react with it. The inhibitor can be, for example, a chemical compound or a protein or fragment of a protein having nuclease inhibitor activity. Examples are antibodies or parts of antibodies which react specifically with a nuclease. Preferably, such an antibody is a monoclonal antibody.

It is possible for the person skilled in the art to find in the literature molecules described as nuclease inhibitors. Described are, for example, antibiotic compounds such as coumermycin or novobiocin, nalidixic or oxolinic acids (Fox and Studzinski, J. Histochem Cytochem. 30 (1982), 364–370), ciprofloxacin (CFL) or norfloxacin (Tempel and Ignatius, Arzneimittelforschung 42 (1992), 1031–1036) and aurintricarboxylic acid (ATA) (Benchokroum et al., Biochem. Pharmacol. 49 (1995), 305–313). More preferably, the nuclease inhibitor is not an acidic molecule and, if it is an acidic molecule, it is administered in a buffered neutral solution. In a preferred embodiment the nuclease inhibitor is an inhibitor of a DNAse I. More preferably, it is a polypeptide or a fragment of a polypeptide which inhibits a DNAse I. In a particularly preferred embodiment the nuclease inhibitor is the globular form of actin (G-actin) (Harwell et al., J. Biol. Chem. 255 (1980), 1210–1220). Several publications have described the ability of G-actin to interact with a large number of actin binding proteins including DNAse I (Sheterline and Sparrow, Protein Profile 1 (1994), 1–121). G-actin binds DNAse I with high affinity and is a potent inhibitor ($K_i$ 1 nM) of DNA hydrolytic activity (Lacks, J. Biol. Chem. 256 (1981), 2644–2648; Pinder and Gratzer, Biochemistry 21 (1982), 4886–4890). Based on these observations, Snabes et al. (J. Biol. Chem. 256 (1981), 6291–6295) have developed an immunoprecipitation assay based on DNAse I/actin binding using rabbit skeletal muscle actin or actin present in tissue and cell extracts. It is known that the interface between DNAse I and G-actin involves two exposed loops in subdomain II (residues P38 to S52) and IV (residues T194 to T203). Thus, a fragment of G-actin used in the scope of the present invention preferably comprises the residues forming these loops. The G-actin may be a naturally occurring form of G-actin, a modified G-actin (Carlier, Biochemistry 31 (1992), 300–309), a polypeptide complexed form (Peitsch et al., EMBO J. 12 (1993), 371–377) or a truncated form as long as the resulting polypeptide retains its ability to inhibit DNAse I activity. The G-actin may be, in principle, of any origin, preferably from vertebrates, more preferably from mammals, e.g. porcine, rabbit, bovine or human origin. G-actin is an ubiquitously expressed polypeptide and can be purified from mainly skeletal muscle and heart or produced by recombinant technology. G-actin is supplied for example by Sigma. The term nuclease inhibitor as used herein also means a nuclease inhibitor as derived from a variety of mammalian species, including, for example, human, simian, rabbit, bovine, porcine or murine. A nuclease inhibitor can be produced, for example, by recombinant technology.

G-actin is known to have further activities, e.g. the capacity to bind divalent metal ions, such as calcium and magnesium ions, and the capacity to bind and hydrolyze ATP, which may cause or contribute to the observed effect of improved introduction of a polynucleotide into cells. Thus, also other proteins having these properties might be useful in the scope of the present invention.

In a preferred embodiment of the use according to the first aspect of the present invention, the prepared therapeutic composition is in a form for administration into a vertebrate tissue. These tissues include those of muscle, skin, brain, lung, liver, spleen, bone marrow, thymus, heart, lymph, bone, cartilage, pancreas, kidney, gall bladder, stomach, intestine, testis, ovary, uterus, rectum, nervous system, eye, gland, connective tissue, blood, tumor etc. Cells where the improved transfection of a foreign polynucleotide would be obtained are those found in each of the listed target tissues (muscular cells, airway cells, hematopoïetic cells, etc.). The administration may be made by intradermal, subdermal, intravenous, intramuscular, intranasal, intracerebral, intratracheal, intraarterial, intraperitoneal, intravesical, intrapleural, intracoronary or intratumoral injection, with a syringe or other devices.

Transdermal administration is also contemplated, as are inhalation or aerosol administration.

In a preferred embodiment, the therapeutic composition is for the introduction into muscle tissue, more preferably, by intramuscular injection routes.

In a preferred embodiment of the first aspect of the present invention, the use of a nuclease inhibitor for the preparation of a therapeutic composition for improving transfection of a polynucleotide into a cell is provided wherein said therapeutic composition is administered independently from a second administration consisting in administration of a composition containing at least one polynucleotide. According to the present invention, the first administration can be done prior to, concurrently with or subsequent to the second administration, and vice-versa. The therapeutic composition administration and second administration can be performed by different delivery routes (systemic delivery and targeted delivery, or targeted deliveries for example). In a preferred embodiment, each should be done into the same target tissue and most preferably by injection.

In a further embodiment of the use according to the present invention, the therapeutic composition further comprises at least one polynucleotide. In a particularly preferred embodiment, the polynucleotide which is contained in the composition, contains and is capable of functionally expressing a gene in said cell.

The polynucleotide may be a DNA or RNA, single or double stranded, linear or circular, natural or synthetic, modified or not (see U.S. Pat. No. 5,525,711, U.S. Pat. No. 4,711,955 or EP-A 302 175 for modification examples). It may be, inter alia, a genomic DNA, a cDNA, an mRNA, an antisense RNA, a ribosomal RNA, a ribozyme, a transfer RNA or DNA encoding such RNAs. "Polynucleotides" and "nucleic acids" are synonyms with regard to the present invention. The polynucleotide may also be in the form of a plasmid or linear polynucleotide which contains at least one expressible sequence of nucleic acid that can generate a polypeptide, a ribozyme, an antisense RNA or another molecule of interest upon delivery to a cell. The polynucleotide can also be an oligonucleotide which is to be delivered to the cell, e.g., for antisense or ribozyme functions. The polynucleotide according to the present invention should preferably be understood as a naked polynucleotide (Wolff et al., Science 247 (1990), 1465–1468) or as a polynucleotide associated or complexed with a viral polypeptide or a cationic compound or with any component which can participate in the uptake of the polynucleotide into the cells (see Ledley, Human Gene Therapy 6 (1995), 1129–1144 for a review). Both DNA or RNA can be delivered to cells to form therein a polypeptide of interest. Preferably, the polynucleotide present in the therapeutic composition is in the form of plasmid DNA. If the polynucleotide contains the proper genetic information, it will direct the synthesis of relatively large amounts of the encoded polypeptide. When the polynucleotide delivered to the cells encodes an immunizing polypeptide, the use according to the invention can be applied to achieve improved and effective immunity against infectious agents, including intracellular viruses, and also against tumor cells. The genetic information necessary for expression by a target cell comprise all the elements required for transcription of said DNA into mRNA and for translation of mRNA into polypeptide. Transcriptional promoters suitable for use in various vertebrate systems are well known. For example, suitable promoters include viral promoters like RSV, MPSV, SV40, CMV or 7.5 k, vaccinia promoter, inducible promoters, etc. The polynucleotide can also include intron sequences, targeting sequences, transport sequences, sequences involved in replication or integration. Said sequences have been reported in the literature and can be readily obtained by those skilled in the art. The polynucleotide can also be modified in order to be stabilized with specific components as spermine.

According to the invention, the polynucleotide can be homologous or heterologous to the target cells into which it is introduced. Advantageously said polynucleotide encodes all or part of a polypeptide, especially a therapeutic or prophylactic polypeptide. A polypeptide is understood to be any translational product of a polynucleotide regardless of size, and whether glycosylated or not, and includes peptides and proteins. Therapeutic polypeptides include as a primary example those polypeptides that can compensate for defective or deficient proteins in an animal or human organism, or those that act through toxic effects to limit or remove harmful cells from the body. They can also be immunity conferring polypeptides which act as endogenous immunogens to provoke a humoral or cellular response, or both. Examples of polypeptides encoded by the polynucleotide are enzymes, hormones, cytokines, membrane receptors, structural polypeptides, transport polypeptides, adhesines, ligands, transcription factors, traduction factors, replication factors, stabilization factors, antibodies, more especially CFTR, dystrophin, factors VIII or IX, E6 or E7 from HPV, MUC1, BRCA1, interferons, interleukin (IL)2, IL-4, IL-6, IL-7, IL-12, GM-CSF (Granulocyte Macrophage Colony Stimulating Factor), the tk gene from Herpes Simplex type I virus (HSV-1), p53 or VEGF. The polynucleotide can also code for an antibody. In this regard, antibody encompasses whole immunoglobulins of any class, chimeric antibodies and hybrid antibodies with dual or multiple antigen or epitope specificities, and fragments, such as $F(ab)_2$, Fab', Fab including hybrid fragments and anti-idiotypes (U.S. Pat. No. 4,699,880).

Furthermore, the invention relates to a composition for the introduction of a polynucleotide into a cell, said composition comprising at least one polynucleotide and at least one nuclease inhibitor. Polynucleotide and nuclease inhibitor components are defined as above.

In a preferred embodiment, the nuclease inhibitor contained in said composition is a DNAse inhibitor and even more preferred, a DNAse I inhibitor. In a particularly preferred embodiment, the nuclease inhibitor is G-actin or a fragment thereof, having the capability to inhibit a DNAse I.

The amount of nuclease inhibitor in the compositions ranges preferably between $4 \times 10^{-5}$ and 4 µg per pg of DNA, preferably between $4 \times 10^{-4}$ and 2 µg per pg of DNA. In a preferred embodiment, said composition comprises between $4 \times 10^{-3}$ and $4 \times 10^{-1}$ µg of nuclease inhibitor per µg of DNA.

In another preferred embodiment, the polynucleotide which is contained in the composition, contains and is capable of functionally expressing, a gene in a cell, preferably in a vertebrate cell. One particularly preferred embodiment of the invention is a composition wherein said polynucleotide is naked. Nevertheless, the polynucleotide comprised in said composition can also be associated with viral polypeptides, or complexed with cationic components, more particularly with cationic lipids. In general, the concentration of polynucleotide in the composition is from about 0.1 µg/ml to about 20 mg/ml.

In a further preferred embodiment the composition further comprises at least one component selected from the group consisting of chloroquine, protic compounds such as propylene glycol, polyethylene glycol, glycerol, ethanol, 1-methyl L-2-pyrrolidone or derivatives thereof, aprotic compounds such as dimethylsulfoxide (DMSO), diethylsulfoxide, di-n-propylsulfoxide, dimethylsulfone, sulfolane, dimethyl-formamide, dimethylacetamide, tetramethylurea, acetonitrile or derivatives. The composition may also advantageously comprise a source of a cytokine which is incorporated in the form of a polypeptide or as a polynucleotide encoding the cytokine. Preferably, said cytokine is interleukin 10 (IL-10). According to a preferred embodiment, the composition comprises 5–15% of DMSO and/or 0.001 to 1 µg preferably 0.01 to 0.1 µg of IL-10.

In a further preferred embodiment the composition according to the first aspect of the invention can be used in a method for the therapeutic treatment of humans or animals. In this particular case, the composition according to the invention may also comprise a pharmaceutically acceptable injectable carrier (for examples, see Remington's Pharmaceutical Sciences, 16$^{th}$ ed. 1980, Mack Publishing Co.). The carrier is preferably isotonic, hypotonic or weakly hypertonic and has a relatively low ionic strength, such as provided by a sucrose solution. Furthermore, it may contain any relevant solvents, aqueous or partly aqueous liquid carriers comprising sterile, pyrogen-free water, dispersion media, coatings, and equivalents or diluents (e.g. Tris-HCL, acetate, phosphate), emulsifiers, solubilizers or adjuvants. The pH of the pharmaceutical preparation is suitably adjusted and buffered.

Further, the present invention also relates to a process for introducing a polynucleotide into cells wherein said process comprises contacting said cells with at least one composition according to the invention. This process may be applied by direct administration of said composition to cells of the animal in vivo, or by in vitro treatment of cells which can be extracted from the animal and then re-introduced into the animal body (ex vivo process). According to the practice of the invention, targeted "cells" and "in vivo administration route" are defined as above described.

The present invention also relates to a process for introducing a polynucleotide into cells wherein said process comprises contacting the cells with said polynucleotide prior to, concurrent with or subsequent to contacting them with a nuclease inhibitor. Preferably, the cells are first contacted with the nuclease inhibitor and afterwards with the polynucleotide. "Nuclease inhibitor", "polynucleotide" and the target cells are defined as above.

Preferably, muscle is used as a site for the delivery and expression of a polynucleotide in a number of therapeutic applications because animals have a proportionately large muscle mass which is conveniently accessed by direct injection through the skin. Accordingly, in a preferred case, the invention concerns a process for introducing a polynucleotide, preferably in naked form, into muscle cells in vivo, comprising the steps of administering in vivo at least a polynucleotide and at least a nuclease inhibitor, preferably G-actin, preferably intramuscularly, whereby the polynucleotide is introduced into muscle cells of the tissue. The polynucleotide may encode a therapeutic polypeptide that is expressed by the muscle cells and eventually secreted into the blood stream after the contacting step to provide therapy to the vertebrate. Similarly, it may encode an immunogenic polypeptide that is expressed by the muscle cells after the contacting step and which generates an immune response, thereby immunizing the vertebrate. One important embodiment of the invention is a process for the treatment of muscular dystrophy wherein said polynucleotide operatively codes for dystrophin. Preferably, the composition is introduced into the muscle tissue.

In a second aspect, the present invention relates to the use of interleukin-10 (IL-10) for the preparation of a therapeutic composition for introducing a polynucleotide into a cell. It was furthermore surprisingly found that the addition of interleukin-10 when transfecting a polynucleotide into vertebrate tissue leads to a dramatic improvement of the transfection efficiency. In particular, it was surprisingly found that if the polynucleotide is injected together with an interleukin-10, e.g., into muscular tissue, the transfection is not only improved in the surrounding of the injection site but also in other areas of the muscle. Thus, the present invention preferably relates to the use of interleukin-10 for the preparation of a pharmaceutical composition for an improved introduction of a polynucleotide into a cell. The term "improved introduction" in the scope of the present invention means, in this regard, a more efficient uptake of a polynucleotide by cells when interleukin-10 is present compared to an introduction performed without interleukin-10. This can be determined by comparing the amount of the polynucleotide taken up without the use of interleukin-10 and comparing this amount with the amount taken up by the cells when using interleukin-10 under the same experimental conditions. Preferably, the improved introduction can be determined by a higher amount of expression of the polynucleotide transferred into the cells when using interleukin-10 in comparison to a situation where no interleukin-10 is used.

Preferably, an improved introduction of the polynucleotide into the cell means that the uptake of the polynucleotide by cells is not only improved at the site of administration of the polynucleotide and interleukin-10 but is also improved in neighboring cells. The therapeutic compositions according to the second aspect of the present invention are particularly useful for the delivery of polynucleotides to cells or tissues of a subject in the scope of a gene therapeutic method but are not limited to such use. The term "gene therapy method" is preferably understood as a method for the introduction of a polynucleotide into cells either in vivo or by introduction into cells in vitro followed by re-implantation into a subject. "Gene therapy" in particular concerns the case where the gene product is expressed in a target tissue as well as the case where the gene product is excreted, especially into the blood stream.

In the scope of the present invention the term "introduction" means the transfer of the polynucleotide into a cell (transfection).

Since its discovery in 1990, interleukin-10 (IL-10), which is a pleiotropic hormone, has been implicated as an important regulator of function of the immune system (Moore et al., Annu. Rev. Immunol. 11 (1993), 165–190). In the scope of the present invention IL-10 is understood to be a cytokine that inhibits cell-mediated immunity and inflammation while promoting humoral responses. Naturally, the cytokine IL-10 is produced by Th0 and Th2 cells, B-lymphocytes, monocytes/macrophages, keratinocytes and bronchial epithelial cells (reviewed by Demoly et al., Gene Ther. 4 (1997), 507–516). In the scope of the present invention IL-10 is preferably understood to have at least one of the following characteristics. It activates both proliferation and viability of B lymphocytes and mast cells, increases E-selectin expression of endothelial cells and neutrophil accumulation at the site of inflammation (Vora et al., J. Exp. Med. 184 (1996), 821–829). Moreover, it increases Bcl-2 expression and survival of hematopoietic progenitor cells (Weber-Nordt et al., Blood 88 (1996), 2549–2548). On the other hand, IL-10 presents also many other properties:

- it enhances resolution of inflammation by promoting clearance of recruited neutrophils through apoptosis (Cox, Am. J. Physiol. 271 (4Pt 1) (1996), L566-L571);
- it downregulates monocyte/macrophages, Langerhans and dendritic cell functions (increases bacteria intracellular survival, lowers cytokine synthesis, oxygen free radical genesis and antigen presentation);
- it indirectly prevents antigen-specific T-cell activation, which is associated with inhibition of MHC class II antigen presentation and accessory cell functions of presenting cells to T cells and NK cells (Powrie and Coffman, Res Immunol. 144 (1993), 639–643; Moore et al., Annu. Rev. Immunol. 11 (1993), 165–190; Murray et al., J. Immunol. 158 (1997), 315–321);
- it inhibits Th1 lymphocyte and neutrophil expansion and the synthesis of their cytokines (IL-2, IFN-γ, IL-3, TNF, GM-CSF) and also eosinophil survival and cytokine production (GM-CSF, TNF-α, IL8);
- it is required to prevent immune hyperactivity during infection with various agents (parasites, bacteria, viruses) (Hunter et al., J. Immunol. 158 (1997), 3311–3116);
- it indirectly suppresses tumor growth and certain tumors by inhibiting infiltration of macrophages which may provide tumor growth promoting activity (Richter et al., Cancer Res. 53 (1993), 4134–4137). Fibrinogen (a potential marker of vascular disease) is also downregulated by IL-10 (Vasse et al., Br. J. Haematol. 93 (1996), 955–961).

These overall properties together with its good tolerability led to the conviction that IL-10 has great potential therapeutic utility in the treatment of diseases, such as chronic inflammation, autoimmune diseases, transplant rejection, graft-versus-host disease, sepsis (de Vries, Ann. Med. 27 (1995), 537–541), asthma (Demoly et al., Gene Ther. 4 (1997), 507–516) and cancer (Richter et al., Cancer Res. 53 (1993), 4134–4137).

Accordingly, many pharmaceutical applications of interleukin-10 have already been described such as for example:

pretreatment with rhIL-10 of patient which reduces endotoxin-induced febrile responses, cytokine responses, and granulocyte accumulation in human lungs (Pajkrt et al., J. Immunol. 158 (1997), 3971–3977). In vivo topical application of IL-10 induces down-regulation of preinflammatory cytokine secretion both systemically and locally in patients with inflammatory bowel disease (Schreiber et al., Gastroenterology 108 (1995), 1434–1444) and psoriasis (Michel et al., Inflamm. Res. 46 (1997), 32–34) In the later example, the IL-10 inducer vitamin D3 (and its analogues) attracted interest as new therapeutic agents;

IL-10 was also shown to attenuates both local and distant organ injury in lung and skeletal muscle (Engles et al., J. Surg. Res. 69 (1997), 425–428);

prolongation of allograft survival can be achieved through gene transfer of gene encoding TGF-β or IL-10 inducing a transient expression of the cytokines within allografts and allowing local immunosuppression while avoiding the systemic toxicity of conventional immunosuppression (Qin et al., Transplantation 59 (1995), 809–816; Fabrega et al., Transplantation 62 (1996), 1866–1871);

IL-10 suppressive action (alone or in combination with IL-4 or TGF-b) on inflammatory or immunostimulant cytokines led to applications for autoimmune diseases such as diabetes (Moritani et al., J. Clin. Invest. 98 (1996) 1851–1859), rheumatoid arthritis (Sugiyama et al., J. Rheumatol. 22 (1995), 2020–2026), systemic lupus erythematosus or multiple sclerosis (Salmaggi et al., J. Neurol. 243 (1996), 13–17). IL-10 is also produced by Schwann cells that provide a constitutive immunosuppressant system for the peripheral nervous system (Jander et al., J. Neurosci. Res. 43 (1996), 254–259). IL-10 may play a role in glial cell differentiation and proliferation (Zocchia et al., Neurochem Int. 30 (1997), 433–439);

IL-10 has been shown to suppress cytokine production and inflammation in various animal models of microbial infection or irritation of various tissues (i.e. digestive track (Herfarth et al., Gut 39 (1996), 836–845); skin (Berg et al., J. Exp. Med. 182 (1995), 99–108); eyes (Hayashi et al., Graefes Arch. Clin. Exp. Ophtalmol. 234 (1996), 633–636) and lung (Grünig et al., J. Exp. Med. 185 (1997), 1089–1099). Intratracheal injection of IL-10 several minutes before allergenic provocation in ovalbumin-sensitized rats significantly inhibits the inflammation process (reviewed by Demoly et al., Gene Ther. 4 (1997), 507–516).

The term "interleukin-10 (IL-10)" as used herein, preferably means a polypeptide having the amino sequence disclosed in Vieira et al. (Proc. Natl. Acad. Sci., 88 (1991), 1172–1176) or in Kim et al. (J. of Immunology 148 (1992) 3618–3623) or a variant of said polypeptide.

An interleukin-10 (IL-10) variant as referred to herein is a polypeptide substantially homologous to a sequence of a native mammalian IL-10 but that has an amino acid sequence different from said native mammalian IL-10 polypeptide because of an amino acid deletion, addition, insertion or substitution. Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu or Ala for one another, or substitutions of one polar residue for another, such as between Lys and Arg, Glu and Asp, or Gln and Asn. Other such conservative substitutions, for example, substitutions of an entire region having similar hydrophobicity characteristics, are well known in the art. Naturally occurring IL-10 variants are also encompassed by the invention.

The term IL-10 as used herein also means IL-10 as derived from a variety of mammalian species, including, for example, human, simian, rabbit, bovine, porcine or murine. IL-10 can be produced by recombinant technology. IL-10 is supplied, for example, by Sigma.

In a preferred embodiment of the use according to the second aspect of the present invention the prepared therapeutic composition is in a form for administration into a vertebrate tissue. These tissues include those of muscle, skin, brain, lung, liver, spleen, bone marrow, thymus, heart, lymph, bone, cartilage, pancreas, kidney, gall bladder, stomach, intestine, testis, ovary, uterus, rectum, nervous system, eye, gland, connective tissue, blood, tumor etc. Cells where the improved transfection of a foreign polynucleotide would be obtained are those found in each of the listed target tissues (muscular cells, airway cells, hematopoietic cells, etc.). The administration may be made by intradermal, subdermal, intravenous, intramuscular, intranasal, intracerebral, intratracheal, intraarterial, intraperitoneal, intravesical, intrapleural, intracoronary or intratumoral injection, with a syringe or other devices. Transdermal administration is also contemplated, as are inhalation or aerosol administration.

In a preferred embodiment, the therapeutic composition is for the introduction into muscle tissue, more preferably, by intramuscular injection routes.

In another preferred embodiment of the second aspect of the present invention, the use of interleukin-10 for the preparation of a therapeutic composition for improving transfection of a polynucleotide into a cell is provided wherein said therapeutic composition is administered independently from a second administration consisting in administration of a composition containing at least one polynucleotide. According to the present invention, the first administration can be done prior to, concurrently with or subsequent to the second administration, and vice-versa. The therapeutic composition administration and second administration can be performed by different or identical delivery routes (systemic delivery and targeted delivery, or targeted deliveries for example). In a preferred embodiment, each should be done into the same target tissue and most preferably by injection.

In a further preferred embodiment of the use according to the present invention, the therapeutic composition further comprises at least one polynucleotide. In a particularly preferred embodiment, the polynucleotide which is contained in the composition, contains and is capable of functionally expressing a gene in said cell.

The polynucleotide may be a DNA or RNA, single or double stranded, linear or circular, natural or synthetic, modified or not (see U.S. Pat. No. 5,525,711, U.S. Pat. No. 4,711,955 or EP-A 302 175 for modification examples). It may be, inter alia, a genomic DNA, a cDNA, an mRNA, an antisense RNA, a ribosomal RNA, a ribozyme, a transfer RNA or DNA encoding such RNAs. "Polynucleotides" and "nucleic acids" are synonyms in the scope of the present invention. The polynucleotide may also be in the form of a plasmid or linear polynucleotide which contains at least one expressible sequence of nucleic acid that can generate a polypeptide, a ribozyme, an antisense RNA or another molecule of interest upon delivery to a cell. The polynucleotide can also be an oligonucleotide which is to be delivered to the cell, e.g., for antisense or ribozyme functions. The polynucleotide according to the second aspect of the present invention should preferably be understood as a naked polynucleotide (Wolff et al., Science 247 (1990), 1465–1468) or as a polynucleotide associated or complexed with a viral polypeptide or a cationic compound or with any component which can participate in the uptake of the polynucleotide into the cells (see Ledley, Human Gene Therapy 6 (1995), 1129–1144 for a review). Both DNA or RNA can be delivered to cells to form therein a polypeptide of interest.

Preferably, the polynucleotide present in the therapeutic composition is in the form of plasmid DNA. If the polynucleotide contains the proper genetic information, it will direct the synthesis of relatively large amounts of the encoded polypeptide. When the polynucleotide delivered to the cells encodes an immunizing polypeptide, the use according to the invention can be applied to achieve improved and effective immunity against infectious agents, including intracellular viruses, and also against tumor cells. The genetic information necessary for expression by a target cell comprise all the elements required for transcription of said DNA into mRNA and for translation of mRNA into polypeptide. Transcriptional promoters suitable for use in various vertebrate systems are well known. For example, suitable promoters include viral promoters like RSV, MPSV, SV40, CMV or 7.5k, vaccinia promoter, inducible promoters, etc. The polynucleotide can also include intron sequences, targeting sequences, transport sequences, sequences involved in replication or integration. Said sequences have been reported in the literature and can be readily obtained by those skilled in the art. The polynucleotide can also be modified in order to be stabilized with specific components as spermine.

According to the invention, the polynucleotide can be homologous or heterologous to the target cells into which it is introduced. Advantageously said polynucleotide encodes all or part of a polypeptide, especially a therapeutic or prophylactic polypeptide. A polypeptide is understood to be any translational product of a polynucleotide regardless of size, and whether glycosylated or not, and includes peptides and proteins. Therapeutic polypeptides include as a primary example those polypeptides that can compensate for defective or deficient proteins in an animal or human organism, or those that act through toxic effects to limit or remove harmful cells from the body. They can also be immunity conferring polypeptides which act as endogenous immunogens to provoke a humoral or cellular response, or both. Examples of polypeptides encoded by the polynucleotide are enzymes, hormones, cytokines, membrane receptors, structural polypeptides, transport polypeptides, adhesines, ligands, transcription factors, traduction factors, replication factors, stabilization factors, antibodies, more especially CFTR, dystrophin, factors VIII or IX, E6 or E7 from HPV, MUC1, BRCA1, interferons, interleukin (IL-2, IL-4, IL-6, IL-7, IL-12, GM-CSF (Granulocyte Macrophage Colony Stimulating Factor), the tk gene from Herpes Simplex type 1 virus (HSV-1), p53 or VEGF. The polynucleotide can also code for an antibody. In this regard, antibody encompasses whole immunoglobulins of any class, chimeric antibodies and hybrid antibodies with dual or multiple antigen or epitope specificities, and fragments, such as $F(ab)_2$, Fab', Fab including hybrid fragments and anti-idiotypes (U.S. Pat. No. 4,699,880).

According to the second aspect the invention relates to a composition for the introduction of a polynucleotide into a cell, said composition comprising at least one polynucleotide and interleukin-10. Polynucleotide and interleukin-10 components are defined as above.

According to the present invention, the amount of interleukin-10 in the compositions ranges preferably between about 0.001 to about 1 µg, preferably from about 0.01 to about 0.1 µg of interleukin-10.

In another preferred embodiment, the polynucleotide which is contained in the composition, contains and is capable of functionally expressing, a gene in a cell, preferably in a vertebrate cell. One particularly preferred embodiment of the invention is a composition wherein said polynucleotide is naked. Nevertheless, the polynucleotide comprised in said composition can also be associated with viral polypeptides, or complexed with cationic components, more particularly with cationic lipids. In general, the concentration of polynucleotide in the composition is from about 0.1 µg/ml to about 20 mg/ml.

In a further preferred embodiment the composition further comprises at least one component selected from the group consisting of chloroquine, protic compounds such as propylene glycol, polyethylene glycol, glycerol, ethanol, 1-methyl L-2-pyrrolidone or derivatives thereof, aprotic compounds such as dimethylsulfoxide (DMSO), diethylsulfoxide, di-n-propylsulfoxide, dimethylsulfone, sulfolane, dimethyl-formamide, dimethylacetamide, tetramethylurea, acetonitrile or derivatives.

In another preferred embodiment the composition according to the invention can be used in a method for the therapeutic treatment of humans or animals. In this particular case, the composition according to the second aspect of the invention may also comprise a pharmaceutically acceptable injectable carrier (for examples, see Remington's Pharmaceutical Sciences, 16$^{th}$ ed. 1980, Mack Publishing Co). The carrier is preferably isotonic, hypotonic or weakly hypertonic and has a relatively low ionic strength, such as provided by a sucrose solution. Furthermore, it may contain any relevant solvents, aqueous or partly aqueous liquid carriers comprising sterile, pyrogen-free water, dispersion media, coatings, and equivalents, or diluents (e.g., Tris-HCl, acetate, phosphate), emulsifiers, solubilizers or adjuvants. The pH of the pharmaceutical preparation is suitably adjusted and buffered.

Furthermore, the present invention also relates to a process for introducing a polynucleotide into cells wherein said process comprises contacting said cells with at least one composition according to the invention. This process may be applied by direct administration of said composition to cells of the animal in vivo, or by in vitro treatment of cells which can be extracted from the animal and then re-introduced into the animal body (ex vivo process). According to the practice of the invention, targeted "cells" and "in vivo administration route" are defined as above described.

The present invention also relates to a process for introducing a polynucleotide into cells wherein said process comprises contacting the cells with said polynucleotide prior to, concurrent with or subsequent to contacting them with interleukin-10. "Interleukin-10", "polynucleotide" and the target cells are defined as above.

Preferably, muscle is used as a site for the delivery and expression of a polynucleotide in a number of therapeutic applications because animals have a proportionately large muscle mass which is conveniently accessed by direct injection through the skin. Accordingly, in a preferred case, the invention concerns a process for introducing a polynucleotide, preferably in naked form, into muscle cells in vivo, comprising the steps of administering in vivo at least a polynucleotide and interleukin-10, preferably intramuscularly, whereby the polynucleotide is introduced into muscle cells of the tissue. The polynucleotide may encode a therapeutic polypeptide that is expressed by the muscle cells and eventually secreted into the blood stream after the contacting step to provide therapy to the vertebrate. Similarly, it may encode an immunogenic polypeptide that is expressed by the muscle cells after the contacting step and which generates an immune response, thereby immunizing the vertebrate. One important embodiment of the invention is a process for the treatment of muscular dystrophy wherein said polynucleotide operatively codes for dystrophin. Preferably, the composition is introduced into the muscle tissue.

The invention has been described in an illustrative manner, and it is to be understood that the terminology which has been used is intended to be in the nature of words of description rather than of limitation. Obviously, many modifications and variations of the present invention are possible in light of the above teachings. It is therefore to be understood that within the scope of the claims, the invention may be practiced otherwise than as specifically described.

The following examples illustrate the invention.

Material and Methods

The following materials and methods are used in the examples.

1. Plasmid/interleukin-10 Composition Intramuscular Administration

Plasmids are prepared according to Bischoff et al. (Analytical Biochemistry 254 (1997), 69–81). The tested interleukin-10s were mixed with the plasmid preparation (pTG11033: CMV promoter, β-globin intron, luciferase cassette; pTG11025: CMV promoter, β-globin intron, dystrophin cassette; both diluted in 0.9% NaCl), prior to intramuscular injection. 25 µg of plasmid are injected per muscle in 5 to 10 week-old C57Bl/10 or mdx mice. The 2 tibialis anterior (right and left) muscles were injected (each muscle was considered as a sample, which means number of samples per condition=2×number of mice per condition).

2. Muscle Biopsies

One week after injection of the composition, mice were killed and the tibialis anterior muscles were retrieved and frozen. Based on the injected vector, either luciferase activity was determined in muscle extracts, or dystrophin expression was evaluated by immunohistochemistry.

3. Luciferase Measurement

Luciferase activity was quantified using a conventional measurement kit (Luciferase Assay System, Promega). Briefly, muscles were ground separately and diluted in 200 µl of reporter lysis buffer (Promega). 10 µl-samples were placed in the 96 well-plates and mixed with 100 µl of substrate. Luciferase activity was expressed as number of RLU emitted per minute.

4. Protein Determination

Proteins were measured on 10 µl samples using a VCA Protein Assay Kit (Pierce).

5. Dystrophin Immunohistochemistry

Muscle samples were frozen in liquid nitrogen-cooled isopentane and stored at −80° C. Immunofluorescence microscopy using anti-dystrophin antibody was performed as follows: serial cryostat transverse sections (5–8 µm) of unfixed muscles were prepared on glass slices, dipped in PBS buffer with 1% mouse serum and incubated for 30 min at room temperature, for saturation of the non specific binding sites. After rinsing (3 times, 5 min) in PBS buffer, slices were dipped in PBS buffer containing 1/500 dilution of anti-dystrophin monoclonal antibody (MANDRA-1, Sigma) and incubated for 90 min at room temperature. Slices were rinsed 3 times for 5 min in PBS, then incubated for 30 min at room temperature with biotin-F(ab')$_2$ goat anti-mouse IgG (H+L) diluted 1/500 in PBS. After rinsing (3 times, 5 min in PBS), preparations were incubated 30 min at room temperature with 1/2000 Streptavidin-FITC (1 mol Streptavidin/4 mol Biotin). Slices were then rinsed and mounted with Mowiol for microscopic evaluation.

6. IFN-β Titration

The ELISA titers were challenged with a biological test. The biological activity of human IFN-β corresponded to the protective effect of IFN-β against VSV infection of WISH cells. The titers were determined according to the dilution of the sample which protects 50% of the cells from VSV cytopathic effect. IFN titers were equivalent between ELISA and biological assays, indicating that the IFN detected corresponds to a functional protein. Following standard IFNs were used to calibrate the assays:

human IFN-β NIH (Stock TG 1995 stored at −20° C.)
human IFN-β from the ELISA kit.

The ELISA test was performed according to the manufacturers recommendation.

EXAMPLE 1

Effect of DNAse Inhibitor on pTG11033 Intramuscular Transfection

Figure 1:
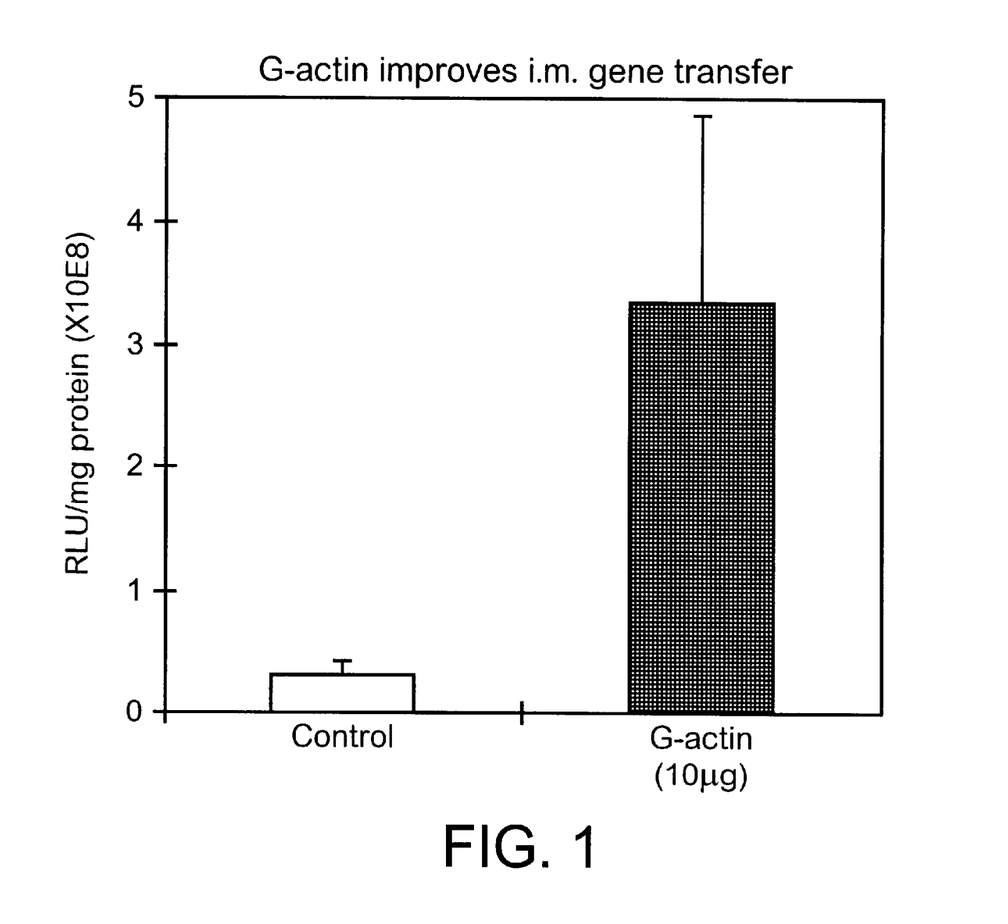
FIG. 1: Effect of DNAse inhibitors on pTG11033 intramuscular transfection. Luciferase activity of mouse right and left tibialis anterior muscles measured 7 days after injection with 25 µg plasmid added with NaCl 0.9% buffer (Control, empty bar) or with 10 µg of G-actin (G-actin, full black bar). Bars are means of RLU (Relative Light Unit) per minute per mg proteins +/- s.e.m. of 8 determinations.

In this example, 10 µg of G-actin were added to pTG11033 (25 µg/muscle) in a total volume of 30 µl to be injected. 4 C57BL/10 adult mice (male and female) per group have been injected in tibialis anterior muscles. The control experiment is performed according to the same condition except that no G-actin is added. The results are presented in FIG. 1. They show that the addition of G-actin leads to a significant increase of intramuscular transfection of the plasmid in muscular cells. This example shows that G-actin increases significantly (about 12 times in the present example) gene transfer into skeletal muscle as evidenced by luciferase activity measurement of the injected muscles 7 days after plasmid administration.

EXAMPLE 2

Combinations of Adjuvants Including G-actin to Improve (i.m.) Transfer of Dystrophin-plasmid (pTG11025)

It was tried to enhance the observed improvement by adding other components to the composition of the invention. In this example, 6 mdx mice were injected (final volume injected: 35 µl) with pTG11025 plasmid preparation added with:

(1) NaCl 0.9%;
(2) IL-10 0.1 µg;
(3) DMSO 10% final;
(4) G-actin 10 µg;
(5) G-actin 10 µg+IL-10 0.1 µg; or
(6) DMSO 10% final+G-actin 10 µg+IL-10 0.1 µg In these experiments, notexin-induced necrosis-regeneration was carried out 3 days prior to plasmid injection (Lefaucheur et Sebille, Neuromuscul. Disord. 5 (1995), 501–509).

Tibialis anterior muscles were collected 7 days after injection, and histological analysis of the transfected tibialis anterior muscle have been conducted. The results (Table I) show the following order of efficiency: 6>4>5>3>2>1

TABLE I

| Tested molecules | Number of dystrophin-positive fibers per cryosection |
|---|---|
| DMSO + G-actin + IL-10 | 89.3 +/− 19.7 |
| G-actin | 71.0 +/− 6.0 |
| G-actin + IL-10 | 44.5 +/− 6.9 |
| DMSO | 37.8 +/− 5.5 |
| IL-10 | 21.7 +/− 1.9 |
| NaCl | 3.3 +/− 0.7 |

Values are mean +/− sem of up to 4 determinations par muscle (obtained from the serial sections of the whole muscles).

In this experiment the best condition (DMSO+G-actin+IL-10) led to around 15% of dystrophin-positive fibers in the mdx tibialis anterior muscles. Interestingly, histological analysis shows that those positive fibers were not localized to a fraction of the muscle (i.e. along the needle track), but homogeneously in the transversal sections. Example 2 (as well as example 3) show that combinations of G-actin and other compounds may act synergistically on gene transfer.

In a second experiment mdx mice were 3 times injected intramuscularly with pTG11025 (dystrophin) plus DMSO, G-actin and IL-10 after notexin-induced muscle regeneration. Plasmid-adjuvant injections were repeated 3 times in raw on a daily basis and dystrophin expression (immunohistochemistry) was evaluated 7 days after the last injection. In this case up to 20% of dystrophin-positive fibers were found in the injected muscles.

EXAMPLE 3

Combinations of Adjuvants Including Interleukin-10 (IL-10) or G-actin to Improve Intracellular Transfer of Luciferase-plasmid (pTG11033)

It was tried to enhance the observed improvement by adding other components to the composition of the invention. In this example, mice were injected (final volume injected: 35 µl) with a pTG11033 (luciferase) plasmid preparation to which the following was added:

1) NaCl 0.9%
2) IL-10 0.1 µg,
3) G-actin 10 µg,
4) DMSO 10% final
5) G-actin 10 µg+IL-10 0.1 µg,
6) DMSO 10% final+G-actin 10 µg+IL-10 0.1 µg
7) G-actin 10 µg+DMSO, 10%
8) DMSO 10%+IL-10

Luciferase activity was measured 7 days after injection of the composition in C57BL/10 mice (4 mice per group).

Figure 2:
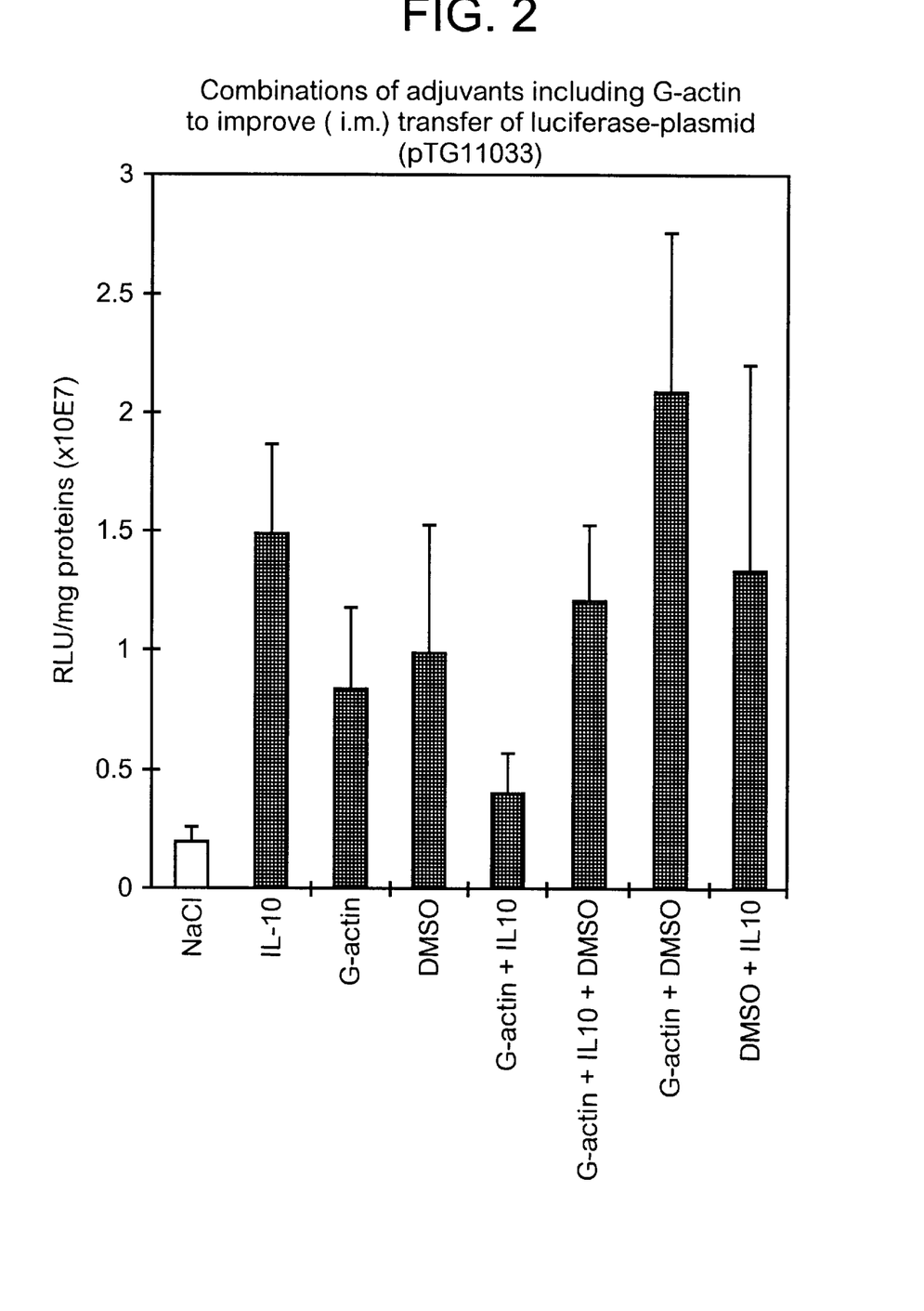
FIG. 2: Combinations of adjuvants including G-actin to improve intramuscular transfer of the luciferase-plasmid (pTG11033). Bars are means of RLU per minute per mg proteins +/- s.e.m of 8 determinations. Luciferase activity was measured 7 days after plasmid injection into C57BL/10 mice (4 mice per group) added with either NaCl 0.9% (empty bars) or different combinations of adjuvants (black bars), NaCl 0.9%, IL-10 0.1 µg, G-actin 10 µg, DMSO 10% final, G-actin+IL-10, or DMSO+G-actin+IL-10, G-actin+DMSO, DMSO+IL-10.

The data show (FIG. 2) that injection of naked DNA in accordance with the present invention (intramuscularly) produced improved expression in muscle which is not limited to the injection site. Thus, one of the fundamental differences between the present invention and the prior art methods is that the present invention results in an increased non-localized gene expression in muscle cells and thus provides the possibility for improving gene expression which is not possible with prior art methods. Furthermore, because of the need for fewer injections for equivalent efficiency, application of the present invention is likely to be better tolerated by patients.

EXAMPLE 4

Dose/Response Effect of G-Actin

Figure 3:
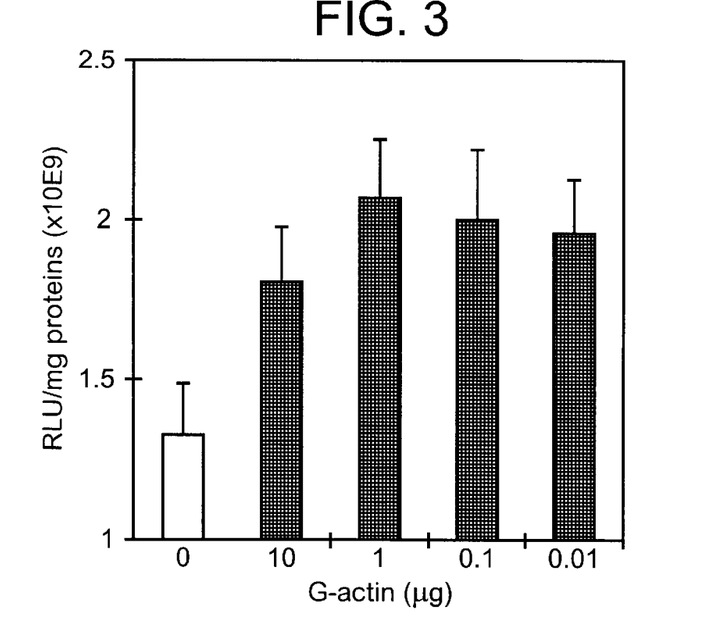
FIG. 3: Dose/Response effect of G-Actin. Luciferase activity of right and left tibialis anterior muscles of 4 mice per group, 7 days after injection with plasmid added with NaCl 0.9% (empty bar) or different doses of G-actin (full black bars). Bars are means of RLU per minute per mg proteins +/- s.e.m. of 8 determinations.

25 μg of plasmid DNA (pTG11033 preparation at 2 mg/ml in 0.9% NaCl) was added with various dilutions (in 0.9% NaCl) of G-actin at final concentrations ranging from 0.01 to 10 μg per 30 μl (final volume), 4 mice per condition. Injections were performed in both right and left tibialis anterior. Luciferase activity was measured in muscles that were collected 7 days after plasmid injection. As shown by FIG. 3, luciferase activity is increased in the muscle that has been injected with plasmid added with G-actin even at low concentrations. Maximal effect seems to be obtained at G-actin concentrations of 0.1 to 1 μg/25 μg plasmid DNA. Bars are mean +/− sem of 8 values per condition.

EXAMPLE 5

Expression of a Gene Encoding a Secreted Protein After Intramuscular Injection of pTG13102 in SCID and C57BL/10 Mice The expression of an IFN-β encoding plasmid pTG13102 was examined after injection into SCID and C57BL/10 mice. Said plasmid is based on the backbone pTG11022 (kanamycin, pCMV, HMG intron, SV40pA, CER and carrying the human IFN-β cDNA). Thus, this plasmid construct shows the same backbone as pTG11033 but the gene encodes the human interferon-beta and allows high level production of huIFN-β in vitro (about 50,000 IU/ml). The huIFN-β plasmid was validated in vitro (calcium phosphate transfection) on the mouse muscle cell line C2C12. huIFN-β was measured using a standardized ELISA kit (Fujirebio). G-actin from porcine muscle (purchased from Sigma, L'Isle d'Abeau Chesnes, France) was diluted at 5 μg/μl in distilled water and stored at −20° C. until use. Plasmid pTG13102 was injected in adult C57BL/10 and SCID mice in the presence of the following adjuvants: G-actin, IL-10, or DMSO. 25 μg plasmid was injected in each of the right and left tibialis anterior (TA) and quadriceps muscles (Quadr.). Six groups of 3 mice were injected 4 times into the right and left TA and Quadr. muscles with 25 μg of pTG131102 in NaCl 0.9% or with a mixture of 10 μg G-actin, 0.1 mM MgCl$_2$ and/or DMSO (10% final). The total volume injected per muscle was 30 μl. Prior to plasmid administration, muscles were treated 3 days by injecting 3ng/25 μl of notexine in order to induce muscle regeneration (which follows the notexin-induced necrosis). Blood samples were taken at various time points. At day 7 and day 14 after plasmid injection, mice were sacrificed and their muscles were dissected. The muscles were collected at the end of the experiment, frozen and grinded. Grinded samples were then extracted using a PBS buffer (600 μl and 400 μl volume for tibialis and quadriceps, respectively). The supernatants were then used for human IFN-β measurement.

Human IFN-β was detected in sera of both SCID (FIG. 5A) and C57BL/10 mice (FIG. 5B) for at least 2 weeks. The similar blood levels of human IFN-β found in both SCID and C57BL/10 indicate that the immunocompetent mice (the C57BL/10 mice) are equally transfected than immunodepressed animals (SCID mice).

Figure 5A:
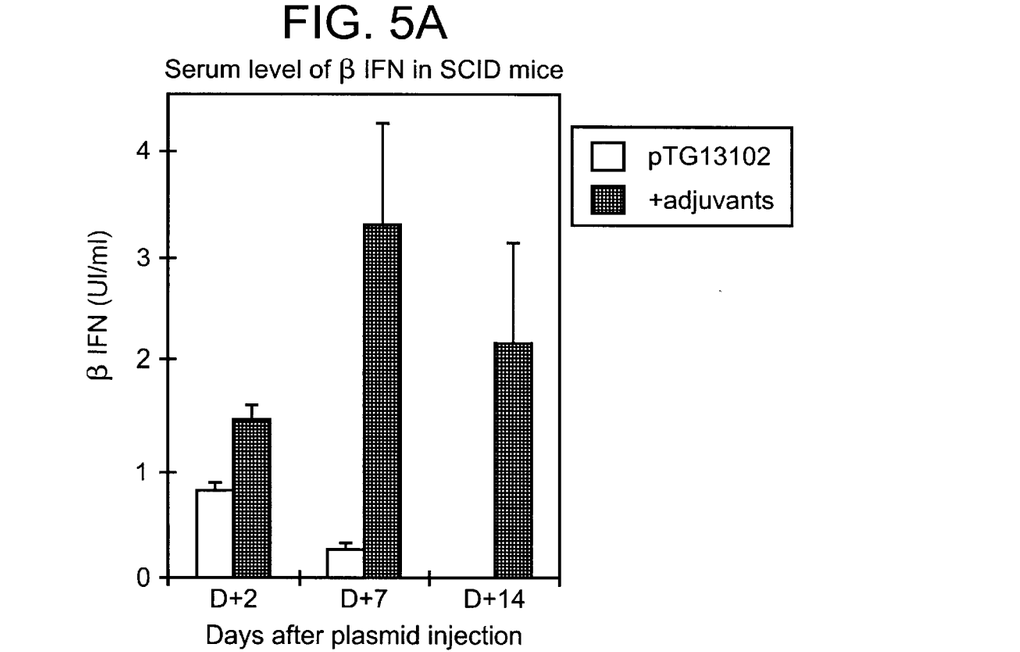
FIG. 5: Detection of human IFN-β in the serum of mice (Panel A: SCID or Panel B: C57BL/10) injected intramuscularly with pTG13102 with our without adjuvants mixture (G-actin, IL-10, DMSO).
Figure 5B:
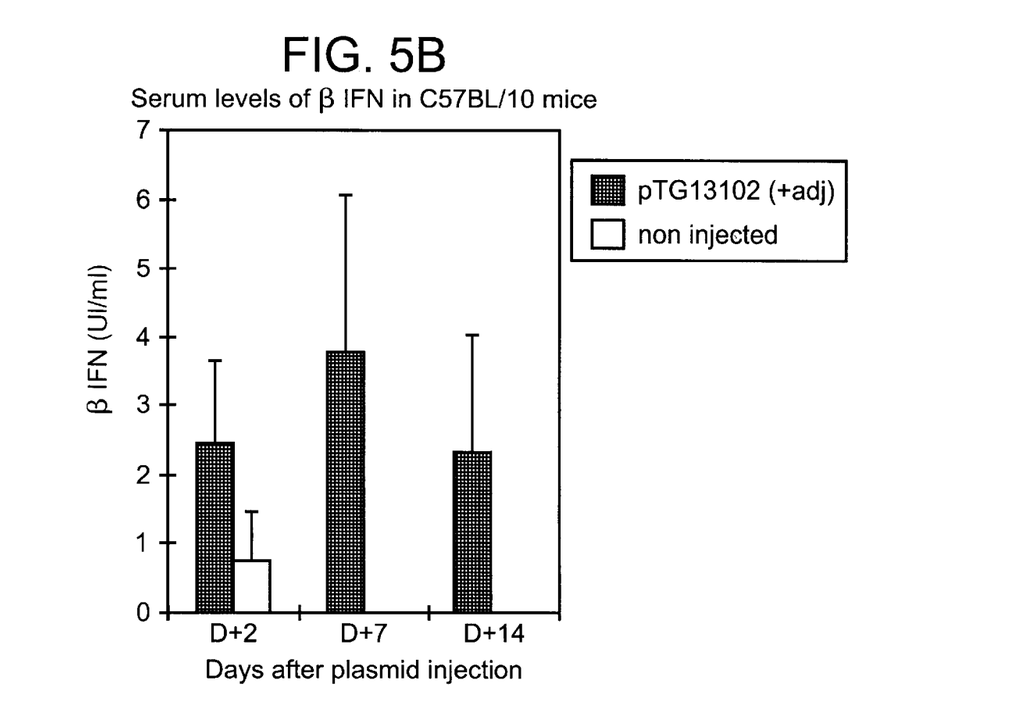

FIG. 5A also demonstrates that higher IFN levels are observed when the plasmid is injected with an adjuvant, while very few if no IFN is expressed in the case of adjuvant-free injected plasmid.

Moreover, the following table shows also that there is a good correlation between IFN levels found in muscles and the corresponding sera (Table 2).

TABLE 2

| | human IFN-β levels found in individual muscles and sera | | | | | | |
|---|---|---|---|---|---|---|---|
| Mouse # (day | | IU/muscle | | | | IU/ml serum | |
| post injection) | INJECTION | Left TA | Right TA | Right Q | Left Q | Day 7 | Day 14 |
| SCID | | | | | | | |
| 1 | pTG13102 | 5 | 4 | 1.2 | | 0.3 | |
| 2 | pTG13102 | 1 | 2 | | | 0.15 | |
| 3 | pTG13102 | 8 | 1 | | | 0.35 | |
| (day 7) | mean | 4.67 | 2.33 | 1.20 | | 0.27 | |
| | sem | 2.03 | 0.88 | | | 0.06 | |
| 4 | pTG13102 + adjuvants | 27 | 36 | 1.02 | | 2.3 | |
| 5 | pTG13102 + adjuvants | 0 | 24 | | 3.9 | 3.4 | |
| 6 | pTG13102 + adjuvants | 23 | 11 | | 1.2 | 1 | |
| (day 7) | mean | 16.67 | 23.67 | 1.02 | 2.55 | 2.23 | |
| | sem | 8.41 | 7.22 | | | 0.69 | |
| 7 | pTG13102 + adjuvants | 6 | 36 | 1 | | 3.6 | 1.33 |
| 8 | pTG13102 + adjuvants | 9 | 2 | | | 0.6 | 0.35 |
| 9 | pTG13102 + adjuvants | 20 | 0 | 0 | 1.62 | 1.6 | 0.9 |
| (day 14) | mean | 11.67 | 12.67 | 0.50 | 1.62 | 1.93 | 0.86 |
| | sem | 4.26 | 11.68 | | | 0.88 | 0.28 |
| C57BL10 | | | | | | | |
| 13 | pTG13102 + adjuvants | 9 | 7 | | | 1.2 | |
| 14 | pTG13102 + adjuvants | 0 | 22 | | | 3.3 | |

TABLE 2-continued human IFN-β levels found in individual muscles and sera

| Mouse # (day post injection) | INJECTION | IU/muscle | | | | IU/ml serum | |
|---|---|---|---|---|---|---|---|
| | | Left TA | Right TA | Right Q | Left Q | Day 7 | Day 14 |
| 15 | pTG13102 + adjuvants | 47 | 4 | | | 1.5 | |
| (day 7) | mean | 18.67 | 11.0 | | | 2.00 | |
| | sem | 14.40 | 5.57 | | | 0.66 | |
| 16 | pTG13102 + adjuvants | 17 | 69 | 2.1 | | 15 | 5.7 |
| 17 | pTG13102 + adjuvants | 18 | 0 | | | 1.5 | 1.4 |
| 18 | pTG13102 + adjuvants | 0 | 1 | | | 0.3 | 0 |
| (day 14) | mean | 11.67 | 23.33 | 2.10 | | 5.60 | 2.37 |
| | sem | 5.84 | 22.84 | | | 4.71 | 1.71 |
| | non injected muscle | 0 | 0 | | | | |
| | non injected muscle | 0 | 0 | | | | |
| | mean | 0 | 0 | | | | |
| | sem | 0 | 0 | | | | |

EXAMPLE 6

Expression of a Reporter Gene Encoding Luciferase After Intramuscular Injection into C57BL/10 Mice The gene expression of a reporter gene encoding luciferase in the presence or absence of G-actin was tested. For this purpose, the molecule(s) being tested was/were injected intramuscularly together with a plasmid preparation of pTG11033 (pCMV-luciferase, same backbone as for pTG13102) in 5 to 10 week old C57BL/10 mice. The preparation was injected into both right and left TA muscles (25 μg plasmid, total volume 30 μl).

Four mice per condition were used. Due to the injections into the right and left tibialis of each mouse 8 samples per condition were obtained. The highest and lowest values were discarded, thus 6 values per condition remained.

Figure 6:
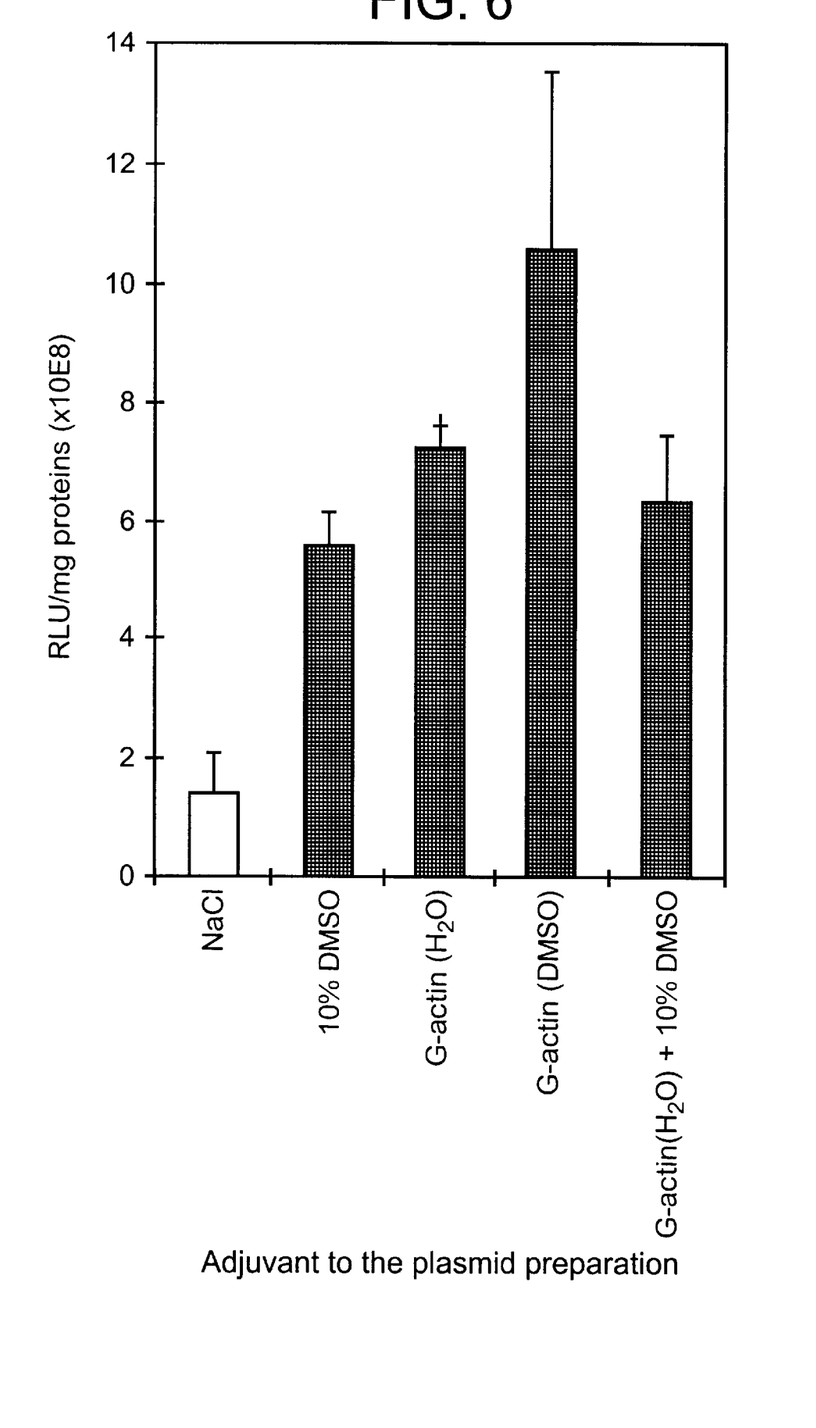
FIG. 6: Luciferase activity in luciferase-plasmid injected mouse muscles is increased by G-actin.

One week after injection of the vectors, the mice were killed and the tibialis anterior muscles were retrieved and frozen. Luciferase activity was determined on muscle extracts. G-actin was diluted either in DMSO (10% final) or in distilled water at 5 μg/μl extemporarily and added to the plasmid preparation alone or together with 10% final DMSO in the case of water-dissolved G-actin. As control, the plasmid alone (prepared in 0.9% NaCl) was injected. The data are shown in FIG. 6.

All adjuvants allowed increased luciferase activity in the injected muscles. G-actin increases gene transfer whether the additive is diluted in water or in DMSO.

EXAMPLE 7

IL-10 Increases Gene Transfer with a Plasmid Comprising the Luciferase Gene 4 groups of 6 C57Bl/10 mice have been injected into the right and left tibialis anterior muscle with 3 different compositions comprising pTG11033 (25 μg/muscle) and 3 various doses of IL-10 (0, 0.1 and 0.01 μg). The control experiment is performed according to the same condition except that no IL-10 is added.

Final volume was 30 μl in NaCl 0.9% solution. The IL-10 used was human recombinant IL-10 (Sigma).

Figure 4:
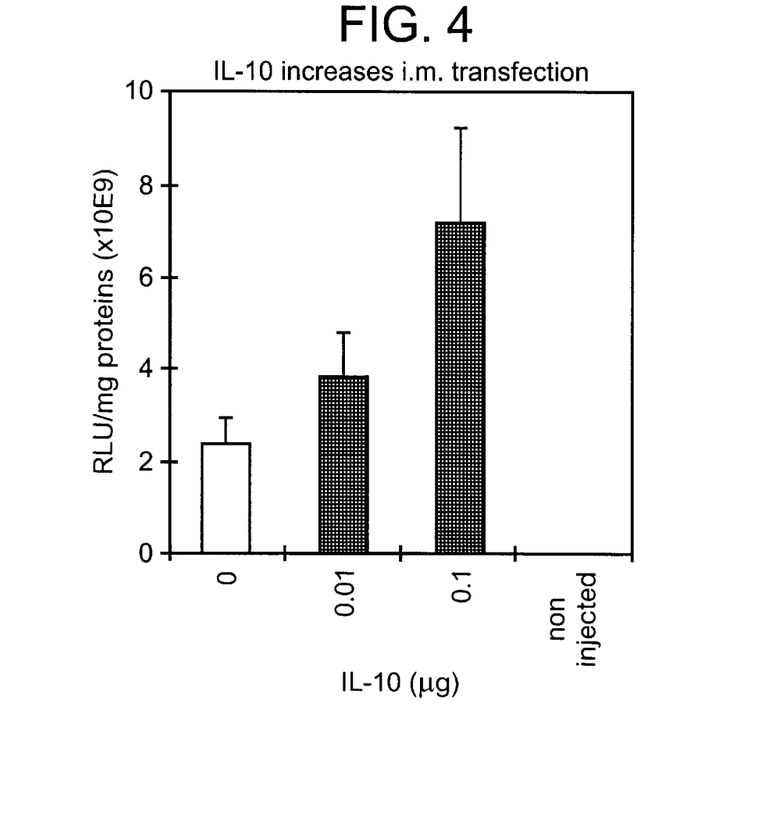
FIG. 4: Effect of Interleukin-10 (IL-10) on pTG11033 intramuscular transfection. Luciferase activity of mouse right and left tibialis anterior muscles measured 7 days after injection with 25 µg plasmid added with NaCl 0.9% buffer (Control, empty bar) or with either 0.01 or 0.1 µg IL-10. Bars are means of RLU (Relative Light Unit) per minute per mg proteins +/- s.e.m. of 12 determinations.

The results are presented in FIG. 4 and show that intramuscular injection of the luciferase plasmid pTG11033 in presence of IL-10 leads to a dose-dependent increase of luciferase expression (factor of 3).

What is claimed is:

1. A method for introducing a polynucleotide into a cell, wherein the improvement comprises administering to the cell a nuclease inhibiting effective amount of a G-actin and a polynucleotide.

2. The method of claim 1, wherein said G-actin is of porcine, rabbit, bovine, simian, murine or human origin.

3. The method of claim 1, wherein said G-actin is for administration into a vertebrate target tissue.

4. The method of claim 3, wherein said administration is made by intradermal, subdermal, intravenous, intramuscular, intranasal, intracerebral, intratracheal, intraarterial, intraperitoneal, intravesical, intrapleural, intracoronary or intratumoral injection.

5. The method of claim 3, wherein said administration is made into the lung by inhalation or aerosol administration.

6. The method of claim 3, wherein said target tissue is muscle.

7. The method of claim 3, wherein the administration of the G-actin is performed independently from a second administration comprising the administration of a composition containing at least one polynucleotide into the same target tissue.

8. The method of claim 7, wherein the administration of the G-actin is performed prior to said second administration.

9. The method of claim 1, wherein the G-actin and the polynucleotide are injected simultaneously.

10. The method of claim 1, wherein said polynucleotide encodes all or part of a polypeptide.

11. A composition for improving the introduction of a polynucleotide into a cell, said composition comprising at least one polynucleotide and at least one G-actin, wherein the polynucleotide is in the form of a plasmid DNA, is associated with viral polypeptides and/or is complexed with cationic components.

12. The composition of claim 11, wherein said G-actin or fragment thereof is of porcine, rabbit, bovine or human origin.

13. The composition of claim 11, wherein said composition contains between $4 \times 10^{-5}$ and 4 μg of G-actin per μg of DNA.

14. The composition of claim 11, wherein the polynucleotide concentration ranges from about 0.1 μg/ml to about 20 mg/ml.

15. The composition of claim 11, wherein said polynucleotide encodes all or part of a polypeptide.

16. The composition of claim 11, wherein said cell is a vertebrate cell.

17. The composition of claim 11, wherein said polynucleotide is naked.

18. The composition of claim 11, wherein said composition further comprises chloroquine.

19. The composition of claim 11, wherein said composition further comprises a pharmaceutically acceptable injectable carrier.

20. A process for improving the introduction of a polynucleotide into cells wherein said process comprises contacting said cells with at least one composition of claim 11 thereby improving the introduction of the polynucleotide into the cells.

21. A process for improving the introduction of a polynucleotide into cells wherein said process comprises either contacting the cells simultaneously with a G-actin and a polynucleotide, contacting the cells first with a G-actin and subsequently with a polynucleotide, or contacting the cells first with a polynucleotide then with a G-actin thereby introducing the polynucleotide into the cells.

22. The composition of claim 11, wherein said composition further comprises at least one component selected from the group consisting of propylene glycol, polyethylene glycol, glycerol, ethanol, and 1-methyl L-2-pyrrolidone.

23. The composition of claim 11, wherein said composition further comprises at least one component selected from the group consisting of dimethylsulfoxide (DMSO), diethylsulfoxide, di-n-propylsulfoxide, dimethylsulfone, sulfolane, dimethylformamide, dimethylacetamide, tetramethylurea, and acetonitrile.

24. The composition of claim 11, wherein said composition further comprises at least one cytokine.

25. The composition of claim 24, wherein said cytokine is interleukin 10 (IL-10).

26. The composition of claim 23, wherein said composition comprises 5–15% of DMSO and/or from about 0.001 to about 1 $\mu$g of IL-10.

* * * * *